(12) United States Patent
Mashino et al.

(10) Patent No.: US 8,344,017 B2
(45) Date of Patent: Jan. 1, 2013

(54) ANTI-HEPATITIS C VIRUS AGENTS AND ANTI-HIV AGENTS

(75) Inventors: Tadahiko Mashino, Tokyo (JP); Kumiko Shimotohno, Tokyo (JP)

(73) Assignees: Mitsubishi Corporation, Tokyo (JP); Tadahiko Mashino, Tokyo (JP); Kumiko Shimotohno, Tokyo (JP)

( * ) Notice: Subject to any disclaimer, the term of this patent is extended or adjusted under 35 U.S.C. 154(b) by 122 days.

(21) Appl. No.: 12/956,505

(22) Filed: Nov. 30, 2010

(65) Prior Publication Data

US 2011/0071202 A1 Mar. 24, 2011

Related U.S. Application Data

(62) Division of application No. 10/548,626, filed as application No. PCT/JP2004/003080 on Mar. 10, 2004, now Pat. No. 7,956,079.

(30) Foreign Application Priority Data

Mar. 10, 2003 (JP) .................................. 2003-63740

(51) Int. Cl.
*A61K 31/40* (2006.01)

(52) U.S. Cl. ........ 514/410; 977/734; 977/735; 977/737; 977/740

(58) Field of Classification Search ........................ None
See application file for complete search history.

(56) References Cited

U.S. PATENT DOCUMENTS

| 5,587,476 A | 12/1996 | Kampe et al. |
| 5,648,523 A | 7/1997 | Chiang |
| 6,265,443 B1 | 7/2001 | Choi et al. |
| 2003/0036562 A1 | 2/2003 | Schinazi et al. |

FOREIGN PATENT DOCUMENTS

| JP | 07-247297 | 9/1995 |
| JP | 8-503593 | 4/1996 |
| JP | 11-255794 | 9/1999 |
| JP | 2000-514412 | 10/2000 |
| JP | 2001-302630 | 10/2001 |

OTHER PUBLICATIONS

Marcorin et al., "Design and Syntehsis of Novel [60]Fullerene Derivatives as Potential HIV Aspartic Protease Inhibitors," Organic Letters, 2000, vol. 2, No. 25, 3955-3958.*
Okuda et al., "Synthesis of Various Water-Solube C60 Derivatives and Their Superoxide-Quencing Activity,"Fullerene Science and Technology, (2000) 8(3) pp. 127-142.*
Mashino et al., "Inhibitory Effect of Fullerene Derivatives on Glutathione Reductase," Fullerene Science and Technology (2001) 9(2), pp. 191-196.*
S. Bosi et al., "Synthesis and Anti-HIV Properties of New Water-Soluble Bis-functionalized [60]fullerene Derivatives", Bioorganic & Medicinal Chemistry Letters, vol. 13, No. 24, pp. 4437-4440, 2003.
N. Gharbi et al., "Chromatographic and Electrophoretic Profiles of Two Acidic Water-Soluble Fullerene Derivatives", Proceedings-Electrochemical Society, vol. 12, pp. 443-450, 2002.
N. Gharbi et al., "Chromatographic Separation and Identification of a Water-Soluble Dendritic Methano [60] fullerene Octadecaacid", Analytical Chemistry, vol. 75, No. 16, pp. 4217-4222, 2003.
D. Schuster et al., "Elevation of the Anti-HIV Potency of a Water-Soluble Dendrimeric Fullerene", Proceedings—Electrochemical Society, vol. 9, pp. 267-270, 2000.
Y. L. Huang et al., "Blockage of Apoptotic Signaling of Transforming Growth Factor-β in Human Hepatoma Cells by Carboxyfullerene", European Journal of Biochemistry, vol. 254, No. 1, pp. 38-43, 1998.
T. Mashino et al., "Antibacterial and Anti-Proliferative Activity of Cationic Fullerene Derivatives", Bioorganic & Medicinal Chemistry Letters, vol. 13, No. 24, pp. 4395-4397, 2003.
S. Bosi et al., "Antimycobacterial Activity of Ionic Fullerene Derivatives", Bioorganic & Medicinal Chemistry Letters, vol. 10, No. 10, pp. 1043-1045, 2000.
D. I. Schuster et al., "Anti-human immunodeficiency virus activity and cytotoxicity of derivatized buckminsterfullerenes", Bioorganic & Medicinal Chemistry Letters, vol. 6, No. 11, Jun. 4, 1996, pp. 1253-1256.

* cited by examiner

*Primary Examiner* — Sreeni Padmanabhan
*Assistant Examiner* — Jody Karol
(74) *Attorney, Agent, or Firm* — Wenderoth, Lind & Ponack, L.L.P.

(57) ABSTRACT

An anti-hepatitis C virus agent or anti-HIV agent comprising, as an active ingredient, a fullerene derivative which has a nitrogen atom forming a ring together with adjacent bonded carbon atom pairs constituting the carbon cluster skeleton of the fullerene or a quaternary amine salt thereof is provided.

1 Claim, No Drawings

ANTI-HEPATITIS C VIRUS AGENTS AND ANTI-HIV AGENTS

This application is a Divisional of U.S. application Ser. No. 10/548,626, filed Jul. 24, 2006 now U.S. Pat. No 7,956,079, which is a national stage application of International application No. PCT/JP2004/003080, filed Mar. 10, 2004.

TECHNICAL FIELD

The invention of this application relates to an anti-hepatitis C virus agent or anti-HIV agent. More particularly, the invention of this application relates to a novel anti-hepatitis C virus or anti-HIV agent comprising a fullerene derivative or a quaternary amine salt thereof as an active ingredient.

BACKGROUND ART

Fullerene, which is a carbon cluster represented by $C_{60}$, is a novel carbon allotrope discovered by Smally, Kroto et al. in 1985. Since a large-scale synthetic method was established in 1990, studies have dramatically progressed in both basic and application fields.

At first, fullerenes were thought to have low chemical reactivity, however, it was shown that various anionic substrates are easily added thereto as an electron deficient olefin. In addition, Diels-Alder reaction, 1,3-dipolar cyclo addition reaction or the like proceeds well to give an adduct attached to the double bond of a conjunction region of 6-membered ring and 6-membered ring of a fullerene.

An effect of such a chemically active novel substance group on a living organism also attracts the interest. For example, with regard to a fullerene derivative, an HIV protease inhibitory activity has been reported for the compound of the following formula (non-patent document 1).

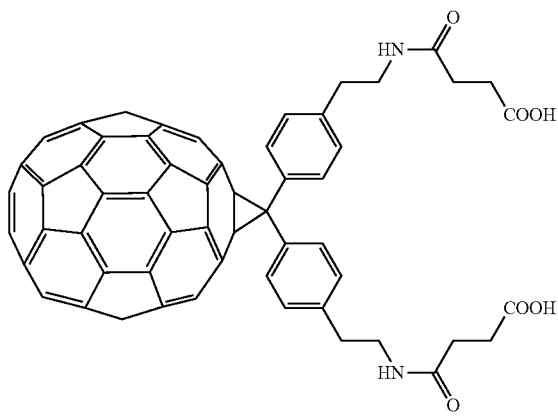 [SMILES: O=C(O)CCC(=O)NCCc1ccc(C2(c3ccc(CCNC(=O)CCC(=O)O)cc3)C3c4cc5c6c7c(cc8ccc9cc%10c%11c%12c(cc(c%13c4c6c(c%13%12)c4c7c8c9c%114)C32)C%10)C5)cc1]

In this situation, a research on a fullerene derivative further having a new bioactivity has been desired, however, in fact, an investigation for application as a bioactive agent has not so much progressed.

Therefore, the inventor of this application synthesized two types of $C_{60}$ fullerene derivatives represented by the following formulae (1) and (2):

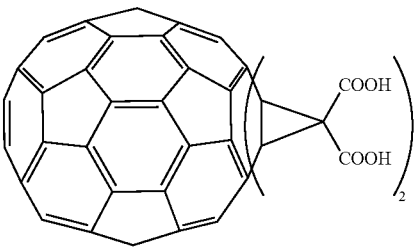

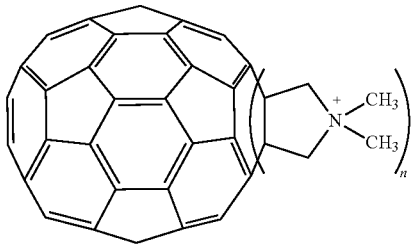

and has investigated their bioactivities. These derivatives have a characteristic that they easily dissolve in an organic solvent (such as DMSO), which is miscible in water, and can be used for a reaction in an aqueous solution.

The inventor first focused on the inhibition of hepatitis C virus RNA polymerase and the inhibition of HIV reverse transcriptase in the process of this investigation.

Hepatitis C virus (HCV) infects through the blood or the like and causes chronic hepatitis. The infected patients are more likely to develop liver cirrhosis or liver cancer, and the natural recovery rate is extremely low. The current therapeutic method is administration of interferon, which is sometimes further combined with ribavirin. However, the elimination rate of HCV is about one-third, which is low. Therefore, development of a new anti-HCV drug has been awaited.

HCV is an RNA virus. After it invades human liver cells, it produces several enzymes from its own RNA by using the protein synthesis system of the host (human) cells. One of these enzymes is HCV RNA polymerase, which is essential for growth of HCV.

It has been reported that if the activity of this RNA polymerase is inhibited, growth of hepatitis C virus can be inhibited, and the virus itself can be eliminated.

On the other hand, AIDS was first reported in 1981, and since then, it has been spread all over the world, which has become a serious social problem. This AIDS is a disease in which the immune system of the body breaks down due to the human immunodeficiency virus (HIV), therefore the patients are susceptible to a variety of infectious diseases and lead to death. HIV is similar to hepatitis C virus and is an RNA virus.

The agents currently used as an AIDS therapeutic drug can be classified into two main categories. One is an inhibitor of the reverse transcriptase that synthesizes DNA from the RNA of HIV, and the other is an inhibitor of the enzyme necessary for growth of HIV (HIV protease, an enzyme that converts a protein synthesized from the virus RNA into an enzyme having an activity). As a reverse transcriptase inhibitor, a nucleoside analogue is mainly used, however, it has a disadvantage in that it is also toxic to human cells. Also, there are few protease inhibitors which are stable in vivo and whose activities are high. In this way, there is no specific drug for AIDS in the present circumstances, and furthermore, the fact that HIV acquires resistance against these drugs has become a big problem.

In this circumstance, as mentioned above, it has been reported that a fullerene derivative has an HIV protease inhibitory activity. At present, various derivatives other than this have been attempted, however, a fullerene derivative having an inhibitory activity against HIV reverse transcriptase has not been reported.

Non-patent document 1: R. F. Schinazi, et al., Antimicrob. Agents Chemother, 37, 1707 (1993)

DISCLOSURE OF THE INVENTION

Based on the background as above, the invention of this application is aimed at providing a novel anti-hepatitis C virus agent having an inhibitory activity against hepatitis C virus RNA polymerase or a novel anti-HIV agent having an inhibitory activity against HIV reverse transcriptase, which contains a fullerene derivative as an active ingredient.

This application provides the following inventions to solve the foregoing problems.

(1) An anti-hepatitis C virus agent or anti-HIV agent, characterized by comprising, as an active ingredient, a fullerene derivative which has a nitrogen atom forming a ring together with adjacent bonded carbon atom pairs constituting the carbon cluster skeleton of the fullerene or a quaternary amine salt thereof.

(2) The foregoing anti-hepatitis C virus agent or anti-HIV agent, characterized in that the nitrogen atom is bonded through a hydrocarbon chain or directly bonded without a hydrocarbon chain to at least any of the adjacent bonded carbon atom pairs.

(3) An anti-hepatitis C virus agent or anti-HIV agent, characterized by comprising, as an active ingredient, a quaternary amine salt of a fullerene derivative which has an organic bond structure represented by the following formula:

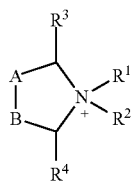

(wherein A and B denote adjacently bonded carbon atoms constituting the carbon cluster skeleton of the fullerene, $R^1$ and $R^2$ are identical or different and denote a hydrocarbon group which may have a substituent, and $R^3$ and $R^4$ are each identical or different and denote a hydrogen atom or a hydrocarbon group which may have a substituent) attached to at least one of the adjacent bonded carbon atom pairs constituting the carbon cluster skeleton of the fullerene is provided.

(4) An anti-hepatitis C virus agent or anti-HIV agent, characterized by comprising, as an active ingredient, a fullerene derivative which has an organic bond structure represented by the following formula:

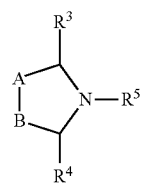

(wherein A and B denote adjacently bonded carbon atoms constituting the carbon cluster skeleton of the fullerene, $R^3$ and $R^4$ are each identical or different and denote a hydrogen atom or a hydrocarbon group which may have a substituent, and $R^5$ denotes a hydrocarbon group which may have a substituent) attached to at least one of the adjacent bonded carbon atom pairs constituting the carbon cluster skeleton of the fullerene.

(5) An anti-hepatitis C virus agent or anti-HIV agent, characterized by comprising, as an active ingredient, a fullerene derivative which has an organic bond structure represented by the following formula:

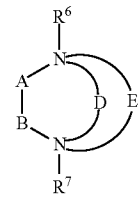

(wherein A and B denote adjacently bonded carbon atoms constituting the carbon cluster skeleton of the fullerene, $R^6$ and $R^7$ are each identical or different and denote a hydrogen atom or a hydrocarbon group which may have a substituent, and D and E are each identical or different and denote a hydrocarbon group which may have a substituent) attached to at least one of the adjacent bonded carbon atom pairs constituting the carbon cluster skeleton of the fullerene or a quaternary amine salt thereof.

(6) An anti-hepatitis C virus agent or anti-HIV agent, characterized in that a hydrocarbon group is a linear chain, branched chain or cyclic hydrocarbon group.

(7) An anti-hepatitis C virus agent or anti-HIV agent, characterized in that a hydrocarbon group is an alkyl group having 1 to 16 carbon atoms.

(8) An anti-hepatitis C virus agent or anti-HIV agent, characterized by comprising, as an active ingredient, at least one kind of carboxyl fullerene derivatives which have an organic bond structure represented by the following formula:

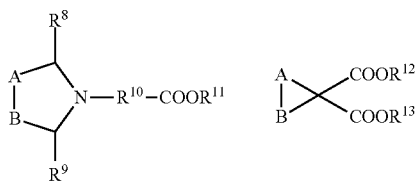

(wherein A and B denote adjacently bonded carbon atoms constituting the carbon cluster skeleton of the fullerene, $R^8$ and $R^9$ are each identical or different and denote a hydrogen atom or a COOR group, R denotes a hydrogen atom or a hydrocarbon group which may have a substituent, $R^{10}$ denotes a hydrocarbon chain which may have a substituent, and the hydrocarbon chain may be bonded through a hetero atom and $R^{11}$, $R^{12}$ and $R^{13}$ are each identical or different and denote a hydrogen atom or a hydrocarbon group which may have a substituent) attached to at least one of the adjacent bonded carbon atom pairs constituting the carbon cluster skeleton of the fullerene.

(9) An anti-hepatitis C virus agent or anti-HIV agent, characterized in that a hydrocarbon chain is a linear chain or branched chain hydrocarbon group.

(10) The anti-hepatitis C virus agent or anti-HIV agent according to any one of the foregoing inventions, characterized in that the fullerene is at least one kind of $C_{60}$ fullerene and higher order fullerenes.

BEST MODE FOR CARRYING OUT THE INVENTION

The invention of this application has characteristics as described above, and the embodiments thereof will be explained below.

An active ingredient of the anti-hepatitis C virus agent or anti-HIV agent of the invention of this application is a fullerene derivative having a structure represented by the foregoing formulae or a quaternary amine salt thereof, or a carboxyl fullerene derivative.

With regard to the fullerene derivative or the quaternary amine salt thereof that is an active ingredient of the anti-hepatitis C virus agent or anti-HIV agent of the invention of this application, in the foregoing formulae, $R^1$ and $R^2$, and $R^5$ are identical or different and denote a hydrocarbon group which may have a substituent, $R^3$ and $R^4$, and $R^6$ and $R^7$ are each identical or different and denote a hydrogen atom or a hydrocarbon group which may have a substituent. Here, as the hydrocarbon group, various kinds of linear or cyclic ones and various kinds of saturated or unsaturated ones are taken into account. Various kinds of aliphatic, alicyclic and aromatic hydrocarbons are taken into account.

Among them, as the hydrocarbon group, a linear chain or a branched chain aliphatic hydrocarbon group is exemplified. In this case, the carbon number is not limited, however, for example, one having about 1 to 16 carbon atoms is preferably exemplified.

In addition, the symbols D and E in the foregoing general formula are each identical or different and denote a hydrocarbon chain which may have a substituent, however, as the hydrocarbon chain in this case, for example, an alkyl chain having 1 to 3 carbon atoms is preferably exemplified.

The substituent that may be bonded to the hydrocarbon group or the hydrocarbon chain may be arbitrary, and for example, an alkoxy group, an acyl group, a carboxyl group, an ester group, an amino group, a substituted amino group, a heterocyclic group and the like are taken into account.

Still furthermore, an anion that is the paring ion of the quaternary amine salt may be various kinds of anions, and can be a pharmacologically acceptable anion. For example, it may be an inorganic acid ion such as a halogen ion or a sulfate ion, or an organic acid ion, or further, a complex ion or the like.

As a fullerene forming the carbon cluster skeleton in the fullerene derivative of the invention of this application, it may be $C_{60}$ or a higher order fullerene such as $C_{70}$ or $C_{82}$.

In the anti-hepatitis C virus agent or anti-HIV agent of the invention of this application, one or more kinds of the fullerene derivatives and the quaternary amine salts thereof as above can be contained as the active ingredients.

With regard to the explanation of synthesis of the fullerene derivative and the quaternary amine salt thereof as the active ingredient of the invention of this application, they can be synthesized, for example, according to the following reaction formula or the like.

$$C_{60} + CH_3NHCH_2CO_2H + RCHO \xrightarrow{toluene}$$

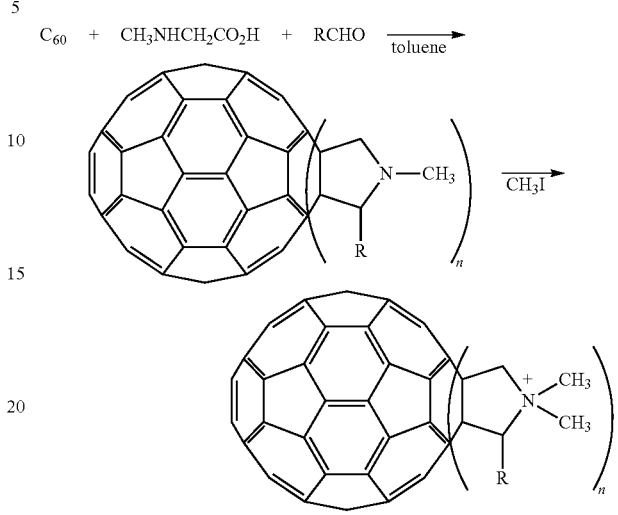

In this reaction formula, by variously changing the kind of aldehyde (RCHO) or by changing the ratio of the reaction materials, the side chain R or the bonding number n can be varied diversely.

In other words, for example, in toluene, $C_{60}$, N-methylglycine and various aldehydes (RCHO) are dissolved, and heated under argon gas flow, whereby an N-methylpyrrolidine derivative is obtained. The reaction time and the amounts of reagents are adjusted according to the number of substituents of a desired derivative. The product is purified with a silica gel column. Subsequently, the reaction is performed in methyl iodide at room temperature, or by heating. In this way, a derivative having various alkyl substituents (R) (a 2-alkyl-N,N-dimethylpyrrolidinium derivative) or a quaternary amine salt thereof can be obtained. Specifically, for example, as described below, fullerene derivatives, in which $R^2$ is H, and $R^4$ is H (compound 2), $C_4H_9$ (compound 3), $C_6H_{13}$ (compound 4) and $C_9H_{19}$ (compound 5), and fullerene derivatives of compound 9, compound 12 and the like are synthesized. It has been confirmed that these are dissolved in DMSO at a concentration of 5 mM or more.

In addition, with regard to the symbols $R^1$ and $R^2$ in the foregoing formula, which is bonded to a nitrogen atom, by using various N-substituted glycines instead of N-methylglycine in the foregoing reaction formula, and by using various reaction materials instead of $CH_3I$, they can be desired ones. For example, the following reaction formula or the like can be followed.

$$C_{60} + C_{10}H_{21}NHCH_2CO_2H + HCHO \xrightarrow{toluene}$$

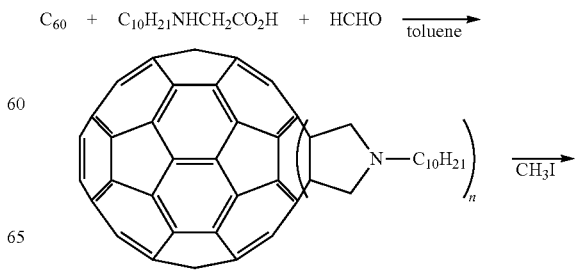

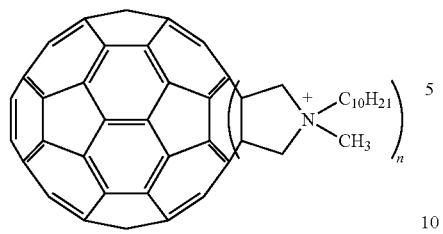

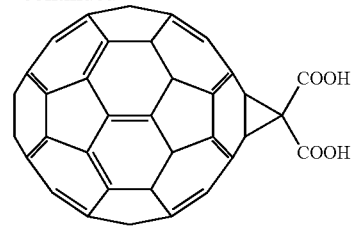

Namely, for example, in toluene, $C_{60}$, N-decylglycine and formaldehyde are dissolved, and heated under argon gas flow, whereby an N-decylpyrrolidine derivative is obtained. The reaction time and the amounts of reagents are adjusted according to the number of n of a desired derivative. The product is purified with a silica gel column. Subsequently, in methyl iodide at room temperature or by heating, a (N-decyl-N-methylpyrrolidinium derivative) can be obtained. Specifically, for example, the compound 6 as described below is synthesized.

In addition, with regard to a compound having hydrocarbon chains D and E in the foregoing formula, for example, it can be easily synthesized by adding $C_{60}$ fullerene and a nitrogen-containing cyclic compound such as piperazine to a solvent such as toluene, and by subjecting the mixture to heating and stirring or the like, and with regard to the quaternary amine salt thereof, it can be easily synthesized by further reacting it with $CH_3I$ or the like. In this way, for example, the compound 11 as described below can be synthesized.

Furthermore, with regard to a carboxyl derivative, for example, the synthetic method is exemplified as follows. <A> Namely, according to the following reaction formula, first, $C_{60}$, diethyl bromomalonate and sodium hydride are added to toluene, and stirred under argon gas flow, whereby a diethyl malonate derivative is obtained. The reaction time and the amounts of reagents are adjusted according to the number of n of a desired derivative. The product is purified with a silica gel column. Subsequently, the diethyl malonate derivative and sodium hydride are added to toluene. Immediately after the solution is heated to reflux, methanol is added, thus a malonate derivative (carboxyl derivative 1) is obtained.

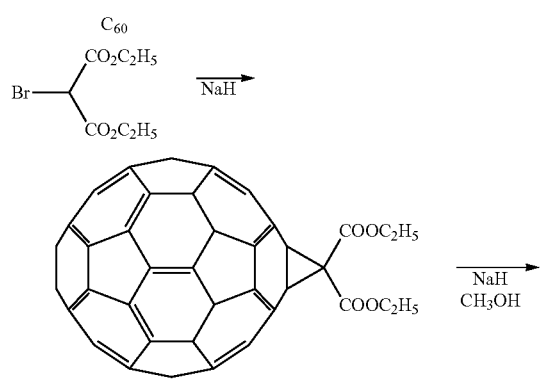

<B> In addition, according to the following reaction formula, first, $C_{60}$ ethyl glyoxylate, iminodiacetic acid diethyl ester and sodium hydride are added to toluene, and heated under argon gas flow, whereby a diethyl derivative is obtained. The reaction time and the amounts of reagents are adjusted according to the number of n of a desired derivative. The product is purified with a silica gel column. Subsequently, the diethyl derivative and sodium hydride are added to toluene. Immediately after the solution is heated to reflux, methanol is added, thus the mentioned derivative (the aftermentioned carboxyl compound 8) is obtained. In this reaction, by changing the iminodiacetic acid diethyl ester to iminomethyl acetic acid ethyl ester, the after-mentioned compound 10 is synthesized. In this way, various compounds can be synthesized.

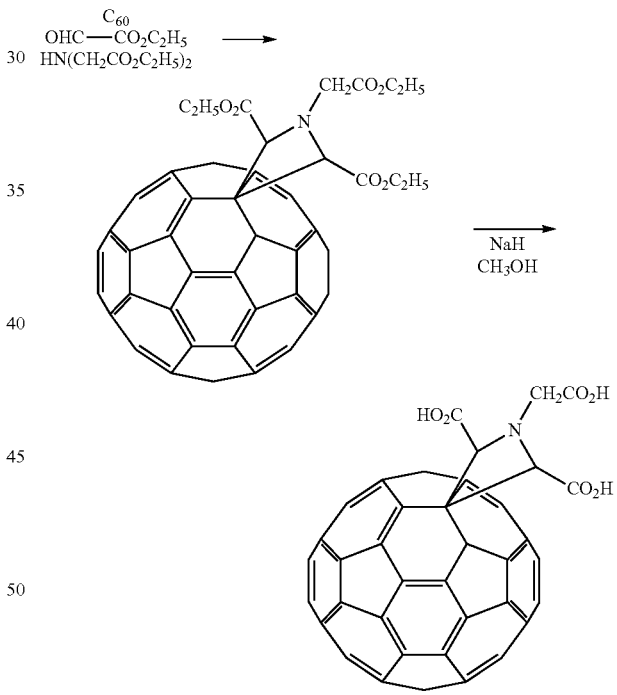

With regard to the carboxyl fullerene derivative as the active ingredient of the anti-hepatitis C virus agent or anti-HIV agent of the invention of this application, the symbols $R^8$ and $R^9$ in the foregoing formula may be the same as the foregoing $R^3$, $R^4$, $R^6$ and $R^7$, the symbol $R^{10}$ is, for example, the same hydrocarbon chain which may have a substituent as mentioned above, and these may be bonded through a hetero atom, for example, an oxygen atom or a nitrogen atom. It can be a linear chain or branched chain hydrocarbon, for example, an alkyl chain. With regard to the number of carbons of the hydrocarbon chain, for example, the range from about 1 to 16 is taken into account.

In addition, the symbols $R^{11}$, $R^{12}$ and $R^{13}$ denote a hydrocarbon group which may have a substituent, and the same ones as mentioned above can be taken into account.

Incidentally, the carboxyl fullerene derivative may be used as a pharmacologically acceptable salt.

With regard to a drug of the invention of this application, the form is not particularly limited, for example, it may be a solid preparation such as a tablet, a granule, a fine granule, a pill, a powder, a capsule, a troche or a chewable tablet, a jelly preparation or an adhesive preparation for external use, a liquid preparation such as an elixir, a syrup, a suspension, an emulsion, an injection or a transfusion.

For preparing a preparation, a common carrier component can be used according to the type of preparation. For example, for preparing a solid preparation, a common component, for example, an excipient such as a saccharide including starch, lactose, sucrose, mannitol, cornstarch and the like, crystal cellulose, carboxymethyl cellulose or light silicic acid anhydride; a binder such as polyvinyl alcohol, polyvinyl pyrrolidone, polyvinyl ether, ethyl cellulose, gum arabic, tragacanth, gelatin, hydroxypropyl cellulose, hydroxypropyl methylcellulose, calcium citrate, dextrin or pectin; a lubricant such as magnesium stearate, calcium stearate, talk, polyethylene glycol or colloid silica; a disintegrator such as starch, carboxymethyl cellulose, calcium carboxymethyl cellulose or croscarmellose sodium, a disintegration aid, a moisturizing agent, a surfactant or the like can be used.

For preparing a liquid preparation, a common component, for example, a solvent such as water for injection, water, ethanol or ethylene glycol, a solubilizing aid such as ethanol, polyethylene glycol, propylene glycol, D-mannitol, cholesterol, triethanolamine, sodium carbonate or sodium citrate, a surfactant such as stearyl triethanolamine, sodium lauryl sulfate, lecithin or glycerin monostearate, a suspending agent for a hydrophilic polymer or the like such as polyvinyl alcohol, polyvinyl pyrrolidone, sodium carboxymethyl cellulose, methyl cellulose, hydroxymethyl cellulose, hydroxyethyl cellulose or hydroxypropyl cellulose, a tonicity adjusting agent such as sodium chloride, glycerin or D-mannitol, a buffering agent such as a phosphate, an acetate, a carbonate or a citrate, a soothing agent such as benzyl alcohol, glucose, an amino acid or the like can be used. For the foregoing solid preparation or liquid preparation, a preservative, a solubilizer, an emulsifier, a dispersant, a thickening agent, a plasticizer, an adsorbent, a flavor, a coloring agent, a corrective, a sweetner, an antiseptic, an antioxidant or the like can be used according to need. The anti-hepatitis C virus agent or anti-HIV agent of the invention of this application can be produced by a common method, for example, such as mixing, kneading, granulating, tableting, coating, sterilizing, emulsifying according to the dosage form of preparation. With regard to production of preparations, each provision of General Rules for Preparations in Japanese Pharmacopoeia can be referred to.

In addition, a drug of the invention of this application may contain other pharmaceutically active substances as long as it contains the foregoing fullerene derivative as the active ingredient.

For example, in the case where it is prescribed as an oral medicine, an antiacid such as sodium hydrogen carbonate, calcium carbonate, magnesium carbonate, magnesium oxide, aluminum hydroxide, aluminum hydroxide gel, magnesium silicate, magnesium aluminosilicate, synthetic aluminum silicate, a coprecipitated product of aluminum hydroxide and sodium hydrogen carbonate, a coprecipitated product of magnesium hydroxide and magnesium carbonate, magnesium aluminometasilicate or dihydroxy aluminum aminoacetate, a stomachic such as gentian, swertia herb, nux vomica, japanese gentian, bitter orange peel, fennel, carnitine chloride, glutamic acid hydrochloride, betaine hydrochloride or bethanechol chloride, a digestive such as pancreatin, pepsin, lemonase chloride, cholic acid, bile powder or dehydrocholic acid, a drug for controlling intestinal function such as mallotus bark, gambir, ubai, cassia seed or geranium herb, an antidiarrheal drug such as loperamide, bismuth subnitrate, bismuth subcarbonate or berberine chloride, an analgesic and antispasmodic such as dicyclomine hydrochloride, scopolamine hydrobromide, atropine methylbromide, scopolamine methylbromide, papaverine hydrochloride, isopropamide iodide, belladonna extract or scopolia extract, a mucosa repairing agent such as sucralfate, sulpiride, gefarnate or teprenone or the like is included. Among these active substances, one or more can be used.

In addition, the drug of the invention of this application may contain, as other anti-hepatitis C virus agents, interferon or ribavirin, and as other anti-HIV agents, a reverse transcriptase inhibitor such as azidothymidine or lamivudine, or a protease inhibitor such as indinavir or saquinavir.

With regard to the drug of the invention of this application, its dose is not particularly limited, however, as a guide, in the case of oral administration, the range between 0.005 and 50 mg per kilogram of body weight per day in divided doses is taken into account.

The fullerene derivative of the invention of this application has low toxicity and is useful as a drug.

Of course, in the invention of this application, human application is taken into account, however, it goes without saying that it may apply to non-human animals.

Therefore, the inventor of this application synthesized compounds such as fullerene derivatives and the quaternary amine salts thereof illustrated in the following table, which are active ingredients of the invention of this application, and evaluated the activities of anti-hepatitis C virus and anti-HIV.

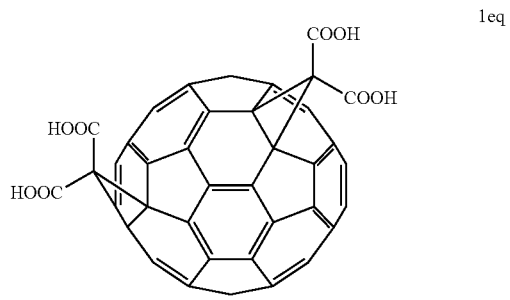

1eq

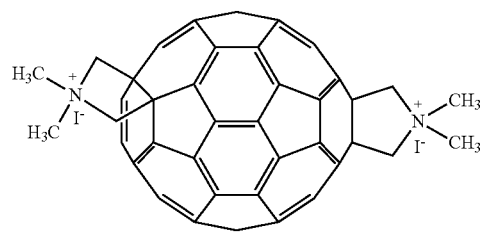

2 t-2

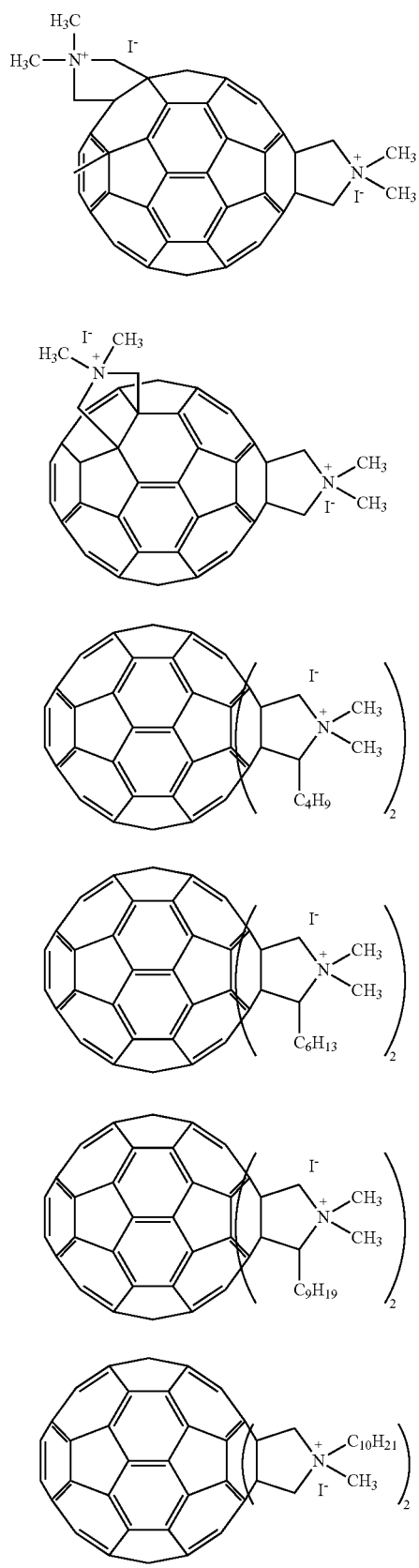
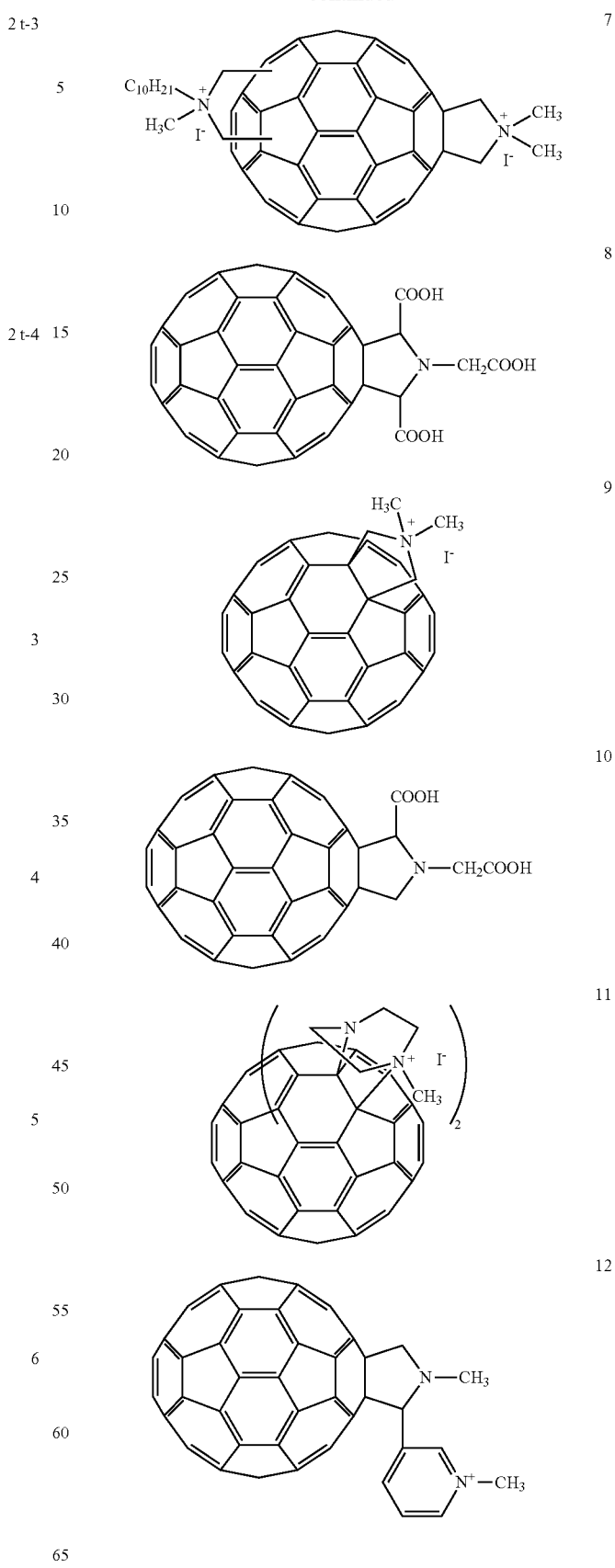
The synthesis examples and the result examples of the activity tests will be explained below.

SYNTHESIS EXAMPLES

1: Synthesis of $C_{60}$-bis(N-methyl-2-hexylpyyrolidine)

In 600 ml of absolute toluene, 200 mg of $C_{60}$ (0.28 mmol) was dissolved, and 50 mg of N-methylglycine (0.56 mmol, 2 equivalent amounts) and 95 mg of heptanal (0.83 mmol, 3 equivalent amounts) were added, then heated to reflux at 135° C. for 3 hours under argon gas flow. The reaction solution was washed with water and saturated saline, dried with sodium sulfate, then the solvent was evaporated under reduced pressure. The obtained solid was purified by silica gel column chromatography (as the eluent, toluene: hexane=5:1, 100% toluene, toluene: ethyl acetate=20:5 were used in this order), thus 25 mg of a regioisomer mixture of $C_{60}$-bis(N-methyl-2-hexylpyyrolidine) (0.025 mmol) was obtained (the yield was 9%).

2: Synthesis of $C_{60}$-bis(N,N-dimethyl-2-hexylpyyrolidinium iodido)

In 5 ml of methyl iodide, 65 mg of $C_{60}$-bis(N-methyl-2-hexylpyyrolidine) (0.065 mmol) was reacted at room temperature by stirring for 24 hours. The precipitated solid was sequentially washed with toluene and ethyl acetate, thus 55 mg of $C_{60}$-bis(N,N-dimethyl-2-hexylpyyrolidinium iodido) (0.043 mmol) was obtained. The yield was 65%.

<Inhibitory Activity>

(1) By using an experimental system for measuring RNA polymerase activity of hepatitis C virus (D. Dhanak et al., J. Biol. Chem., 277, 38322-38237 (2002)), its inhibitory activity was examined.

With regard to the foregoing compound 2, major regioisomers were separated and purified, however, with regard to others, bioactivities were investigated using mixtures.

The results are shown in Table 1. The compound 2 shows the highest inhibitory activity, and a significant difference was not observed among the regioisomers.

TABLE 1

| | Fullernene derivative compound | | | | | | |
|---|---|---|---|---|---|---|---|
| | 1 | 2t-2 | 2t-3 | 2t-4 | 5 | 7 | 8 |
| 50% inhibition concentration (μM) | 3.0 | 0.27 | 0.31 | 0.34 | 1.6 | 1.8 | 2.0 |

There is only one report concerning a compound having an inhibitory activity against RNA polymerase of hepatitis C virus, which was published in fall 2002 (D. Dhanak et al., J. Biol. Chem., 277, 38322-38327 (2002)). The compound is shown in the following formula. The 50% inhibition concentration is 0.08 μM, which is slightly better than that of our derivatives, however, it can be said that they are almost equal. A fullerene derivative is the second hepatitis C virus RNA polymerase inhibitor in the world, and shows promise as a novel anti-hepatitis C virus drug whose structure is totally different from that of the compound represented by the following formula, which is conventionally known.

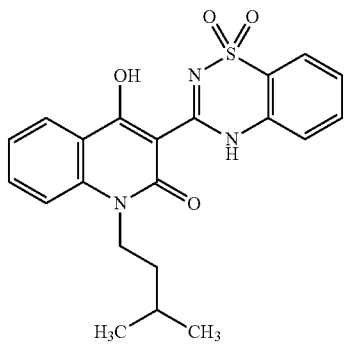 [SMILES: CC(C)CCn1c(=O)c(C2=NS(=O)(=O)c3ccccc3N2)c(O)c2ccccc21]

(2) In addition, since HIV reverse transcriptase is one of the RNA polymerases, the inventor examined its inhibitory activity.

The experiment was performed as follows in 50 mM Tris-HCl buffer (pH 8.3); to 10 μL of a reaction solution which had been prepared so as to contain 30 mM NaCl, 10 mM MgCl, 2.5 mM DTT, 1.25 μg/mL poly(rA). oligo(dT) 12-18, 250 nM dTTP, $^{32}$P-dTTP (800 μCi/mmol), 1 μl of a sample dissolved in DMSO, 1 μl of HIV reverse transcriptase (0.01 U/mL) were added, and the total volume was made up to 20 μl. After the solution was incubated for 1 hour at 37° C., 10 μl of the reaction solution was placed on a Whatman DE81 filter, which was washed three times with $Na_2HPO_4$, once with 70% ethanol and once with ethanol. The dried filter was placed in a vial, and the radioactivity was counted by the liquid scintillation measurement method, which was assigned to the HIV reverse transcriptase activity.

The results are shown in Table 2. It has been confirmed that the active ingredient of the invention of this application inhibits the reverse transcriptase. A reverse transcriptase inhibitor, AZT, which is used as an anti-AIDS drug, is a nucleoside analogue, therefore, by the invention of this application, a novel reverse transcriptase inhibitor which is different from a conventional one is provided.

In addition, it shows a higher inhibitory activity against HIV reverse transcriptase compared with those of delavirdine and nevirapine (F. M. Uckun et al., Bioorg. Med. Chem. Lett., 1999, 9, 2721-2726), which are currently used anti-HIV drugs as the one having the same site of action.

TABLE 2

| Fullernene derivative | 1 | 2 (isomer mixture) | 3 | 4 | 5 |
|---|---|---|---|---|---|
| $IC_{50}$ (μM) | 1.2 | 1.0 | 1.1 | 0.8 | 0.5 |
| Fullernene derivative | 6 | 7 | 8 | 9 | 10 | 11 | 12 |
| $IC_{50}$ (μM) | 8.9 | 1.3 | 0.029 | 1.6 | 1.0 | 2.2 | 5.2 |

<Antimicrobial Activity>

Furthermore, what is emphasized in the invention of this application is that a fullerene derivative or the like used as the active ingredient in the invention of this application has an antimicrobial activity.

In particular, when people is infected with HIV, the immune system breaks down, thereby becoming susceptible to various infectious diseases to result in death, therefore, there are many cases where an antimicrobial drug is used together with an anti-HIV agent for a patient with AIDS. Accordingly, the fullerene derivative or the like of the invention of this application is superior to other anti-HIV drugs because it also has an antimicrobial activity.

For example, as the antimicrobial activity of the active ingredient of the invention of this application as above, it is shown in Table 3.

Incidentally, with regard to the foregoing compound 2, major regioisomers were separated and purified, however, with regard to others, bioactivities were investigated using mixtures.

Table 3 shows the minimum concentration (MIC) of each fullerene derivative or the like which inhibits the growth of various gram positive bacteria in comparison with that of vancomycin (VCM) (the lower the concentration is (small numerical value), the higher the activity is). Each fullerene derivative or the like was dissolved in DMSO, then added to the culture medium of bacteria. Vancomycin is an antimicrobial agent used for drug resistant bacteria (Methicillin resistant strains, MRSA) which has been in trouble now. The regioisomers of the compound 2, 2t-2, 2t-3 and 2t-4, and the compounds 3 and 4 showed an effective antimicrobial activity, however, the activities of the compounds 3 and 4 were somewhat lower than those of the regioisomers of the compound 2. Among the regioisomers of the compound 2, 2t-2, 2t-3 and 2t-4, differences in the effects are observed in some degree depending on bacteria, however, there are no significant differences, and they have an antimicrobial activity substantially equivalent to that of vancomycin, and are also effective for MRSA. Furthermore, worthy of special mention is the fact that these fullerene derivatives and the like show an effective antimicrobial activity against also vancomycin-resistant bacteria (VRE). In addition, the fact that there are no differences among the regioisomers of the compound 2 indicates that the regioisomers of the other compounds do not need to be separated. At present, vancomycin-resistant bacteria began to emerge, therefore, the compound 2 is expected to exert an effect on these.

TABLE 3

| MIC (mg/mL) of fullerene for gram positive bacteria | | | | | | |
|---|---|---|---|---|---|---|
| | 2t-2 | 2t-3 | 2t-4 | 3 | 4 | VCM |
| S. aureus 209P JC-1 | 1.56 | 0.78 | 3.12 | 6.25 | 6.25 | 1.56 |
| S. aureus M133 (MRSA) | 0.78 | 1.56 | 3.12 | 6.25 | 12.5 | 1.56 |
| S. aureus M126 (MRSA) | 3.12 | 1.56 | 3.12 | 6.25 | 12.5 | 1.56 |
| S. eidermidis ATCC 14990 | 6.25 | 3.12 | 3.12 | 6.25 | 12.5 | 3.12 |
| E. hirae ATCC 8043 | 12.5 | 6.25 | 6.25 | 6.25 | 25 | 3.12 |
| E. faecalis W-73 | 12.5 | 6.25 | 6.25 | 6.25 | 50 | 3.12 |
| E. faecium vanA (VRE) | 12.5 | 6.25 | 6.25 | 12.5 | 12.5 | >100 |
| E. faecalis NCTC 12201 (VRE) | 12.5 | 3.12 | 6.25 | 6.25 | 25 | >100 |

Advantage of the Invention

As described above, by the invention of this application, a novel anti-hepatitis C virus agent having an inhibitory activity against hepatitis C virus RNA polymerase or a novel anti-HIV agent having an inhibitory activity against HIV reverse transcriptase, which contains a fullerene derivative or a carboxyl fullerene derivative as an active ingredient is provided.

The invention claimed is:

1. A method for treating Human Immunodeficiency Virus (HIV), comprising administering $C_{60}$ a fullerene derivative which has an organic bond structure represented by the following formula:

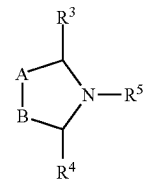

wherein A and B denote adjacently bonded carbon atoms constituting a carbon cluster skeleton of a $C_{60}$ fullerene, $R^3$ and $R^4$ are each the same or different and denote a hydrogen atom or a hydrocarbon group which may have a substituent, and $R^5$ denotes a hydrocarbon group which may have a substituent, attached to at least one of the adjacent bonded carbon atom pairs constituting the carbon cluster skeleton of the $C_{60}$ fullerene, to a patient in need thereof.

* * * * *